US012653546B2

(12) United States Patent
Ali et al.

(10) Patent No.: US 12,653,546 B2
(45) Date of Patent: Jun. 16, 2026

(54) LIGAMENT MODELING AND BALANCING

(71) Applicant: Mako Surgical Corp., Weston, FL (US)

(72) Inventors: Azhar Ali, West Orange, NJ (US); Emily Hampp, Far Hills, NJ (US); Xiangyi Liu, Mahwah, NJ (US); Ormonde Mahoney, Athens, GA (US)

(73) Assignee: Mako Surgical Corp., Weston, FL (US)

( * ) Notice: Subject to any disclaimer, the term of this patent is extended or adjusted under 35 U.S.C. 154(b) by 529 days.

(21) Appl. No.: 17/941,620

(22) Filed: Sep. 9, 2022

(65) Prior Publication Data

US 2023/0080908 A1     Mar. 16, 2023

Related U.S. Application Data

(60) Provisional application No. 63/242,780, filed on Sep. 10, 2021.

(51) Int. Cl.
| | |
|---|---|
| *A61B 17/15* | (2006.01) |
| *A61B 17/17* | (2006.01) |
| *A61F 2/38* | (2006.01) |

(52) U.S. Cl.
CPC ........ *A61B 17/155* (2013.01); *A61B 17/1764* (2013.01); *A61F 2/3859* (2013.01)

(58) Field of Classification Search
CPC .. A61B 17/155; A61B 17/1764; A61F 2/3859
See application file for complete search history.

(56) References Cited

U.S. PATENT DOCUMENTS

| | | | |
|---|---|---|---|
| 6,205,411 | B1 | 3/2001 | DiGioia, III et al. |
| 8,126,533 | B2 | 2/2012 | Lavallee |
| 8,241,016 | B2 | 8/2012 | Laufer et al. |
| 8,880,152 | B2 | 11/2014 | Lavallee |
| 8,990,052 | B2 | 3/2015 | Lavallee et al. |
| 9,050,132 | B2 | 6/2015 | Lavallee |
| 9,220,571 | B2 | 12/2015 | Lavallee |
| 9,684,768 | B2 | 6/2017 | Lavallee et al. |
| 9,741,263 | B2 | 8/2017 | Iannotti et al. |
| 10,198,968 | B2 | 2/2019 | Imhauser et al. |
| 10,285,683 | B2 | 5/2019 | Plaskos et al. |
| 10,321,904 | B2 | 6/2019 | Plaskos et al. |
| 10,441,437 | B2 | 10/2019 | Lavallee |
| 11,000,382 | B1 * | 5/2021 | Cole .................... A61B 5/1121 |
| 2005/0119661 | A1 | 6/2005 | Hodgson et al. |
| 2005/0234332 | A1 | 10/2005 | Murphy |
| 2015/0106024 | A1 | 4/2015 | Lightcap et al. |
| 2018/0033338 | A1 | 2/2018 | Iannotti et al. |

(Continued)

*Primary Examiner* — Sameh R Boles
(74) *Attorney, Agent, or Firm* — Lerner David LLP

(57) ABSTRACT

Disclosed herein are methods for determining resection depths for a knee arthroplasty procedure. The method may comprise the steps of determining a joint translation threshold, determining a joint translation of the femur with respect to the tibia during a joint gap measurement, setting a final joint gap measurement and determining knee resection depths based on the final joint gap measurement. The joint translation threshold may be defined as a translation distance of a femur with respect to a tibia. The joint translation may be less than or equal to the joint translation threshold.

8 Claims, 18 Drawing Sheets

100

(56)                    References Cited

U.S. PATENT DOCUMENTS

| | | | |
|---|---|---|---|
| 2018/0132949 A1 | 5/2018 | Merette et al. | |
| 2018/0140232 A1 | 5/2018 | Fleig et al. | |
| 2019/0008501 A1 | 1/2019 | Plaskos et al. | |
| 2022/0031473 A1* | 2/2022 | Carter | A61B 34/10 |
| 2023/0172600 A1* | 6/2023 | Dumpe | A61B 34/20 |
| | | | 606/90 |

* cited by examiner

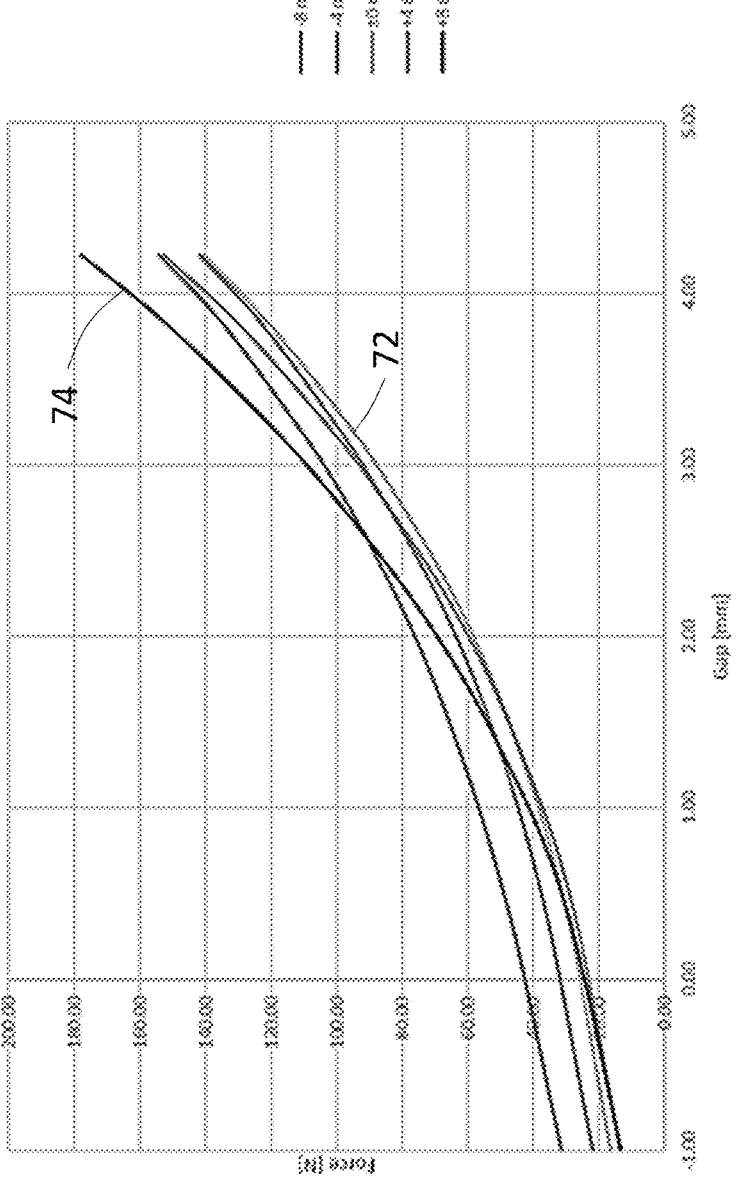
FIG. 5

Table 5. Mean knee flexion patients (degrees) trajectories of pre and early post-operative clinical exams

| | Conventional (n=33) | 3D Reconst. (n=44) | Difference (95% CI) | p-value |
|---|---|---|---|---|
| Extension | | | | |
| Preop | 4.3 | 2.6 | -1.7 (-3.1, 0.2) | 0.027 |
| 6 wks postop* | 0.5 | 0.6 | 0.1 (-0.5, 0.8) | 0.679 |
| Change* | -3.9 | -1.9 | 2.0 (0.3, 3.8) | 0.025 |
| Flexion | | | | |
| Preop | 109.4 | 110.5 | 1.1 (-3.5, 5.7) | 0.639 |
| 6 wks postop* | 104.3 | 112.5 | 8.2 (0.8, 15.6) | 0.030 |
| Change* | -4.1 | 2.0 | 6.1 (2.0, 24.2) | 0.139 |

*6 wks knee motion data was unavailable for the first 5 conventional instrument group patients who followed a different early follow-up schedule; CI = confidence interval

LIGAMENT MODELING AND BALANCING

CROSS-REFERENCE TO RELATED APPLICATION

The present application claims the benefit of the filing date of U.S. Provisional Patent Application No. 62/242,780, filed on Sep. 10, 2021, the disclosure of which is hereby incorporated herein by reference.

FIELD OF THE DISCLOSURE

The present disclosure relates to a system and a method for performing orthopedic procedures, and in particular to a system and a method for performing joint replacement procedures.

BACKGROUND OF THE DISCLOSURE

Anatomic relationship between the femur and tibia is generally maintained during pre-resection total TKA joint assessments as meniscus, ligaments, and articular surfaces are intact. However, if the joint is tensioned after partial or all bone cuts are made, the femur will typically demonstrate a non-native translation relative to the tibia. This is especially true when the knee is placed in flexion causing the tibia to translate posteriorly along the long axis of the femur.

Such a non-native translation of the femur relative to the tibia can lead to improper extension or flexion gap measurements, which can in turn lead to improper implant sizing, implant positioning, bone cuts, etc.

Thus, improved systems and methods for performing joint replacement procedures are desired.

BRIEF SUMMARY OF THE DISCLOSURE

In certain embodiments, the present disclosure relates generally to a system configured to assist in joint balancing procedures by alerting a surgeon when the femur-tibia translation is beyond a pre-determined acceptable threshold during joint distraction and assessment.

In an aspect of the present disclosure, a method of determining resection depths for a knee arthroplasty procedure is disclosed. A method according to this aspect may include the steps of determining a joint translation threshold, determining a joint translation of a femur with respect to a tibia during a joint gap measurement, making a final joint gap measurement, and determining knee resection depths based on the final joint gap measurement. The joint translation threshold may be defined as a translation distance of the femur with respect to the tibia. The joint translation may be less than or equal to the joint translation threshold.

Continuing in accordance with this aspect, the joint translation may be defined as a distance between a femoral axis and a tibial axis. The femoral axis may be any of a femoral mechanical axis and a femoral anatomical axis. The tibial axis may be any of a tibial mechanical axis and a tibial anatomical axis.

In another aspect of the present disclosure, a method of implant selection for a knee arthroplasty procedure is disclosed. A method according to this aspect may include the steps of determining a joint translation threshold, determining a joint translation of a femur with respect to a tibia during a joint gap measurement, making a final joint gap measurement, and determining an implant based on the final joint gap measurement. The joint translation threshold may be defined as a translation distance of the femur with respect to the tibia. The joint translation may be less than or equal to the joint translation threshold.

Continuing in accordance with this aspect, the joint translation may be defined as a distance between a femoral axis and a tibial axis. The femoral axis may be any of a femoral mechanical axis and a femoral anatomical axis. The tibial axis may be any of a tibial mechanical axis and a tibial anatomical axis.

In another aspect of the present disclosure, a method of determining implant placement for a knee arthroplasty procedure is disclosed. A method according to this aspect may include the steps of determining a joint translation threshold, determining a joint translation of a femur with respect to a tibia during a joint gap measurement, making a final joint gap measurement, and determining an implant placement location based on the final joint gap measurement. The joint translation threshold may be defined as a translation distance of the femur with respect to the tibia. The joint translation may be less than or equal to the joint translation threshold.

Continuing in accordance with this aspect, the joint translation may be defined as a distance between a femoral axis and a tibial axis. The femoral axis may be any of a femoral mechanical axis and a femoral anatomical axis. The tibial axis may be any of a tibial mechanical axis and a tibial anatomical axis.

BRIEF DESCRIPTION OF THE DRAWINGS

A more complete appreciation of the subject matter of the present disclosure and the various advantages thereof may be realized by reference to the following detailed description, in which reference is made to the following accompanying drawings:

FIG. 5 is a graph showing simulated force and joint gap at various joint translations;

FIG. 15 is a table showing mean post-operative knee flexion and extension;

DETAILED DESCRIPTION

Figures 1A, 1B:
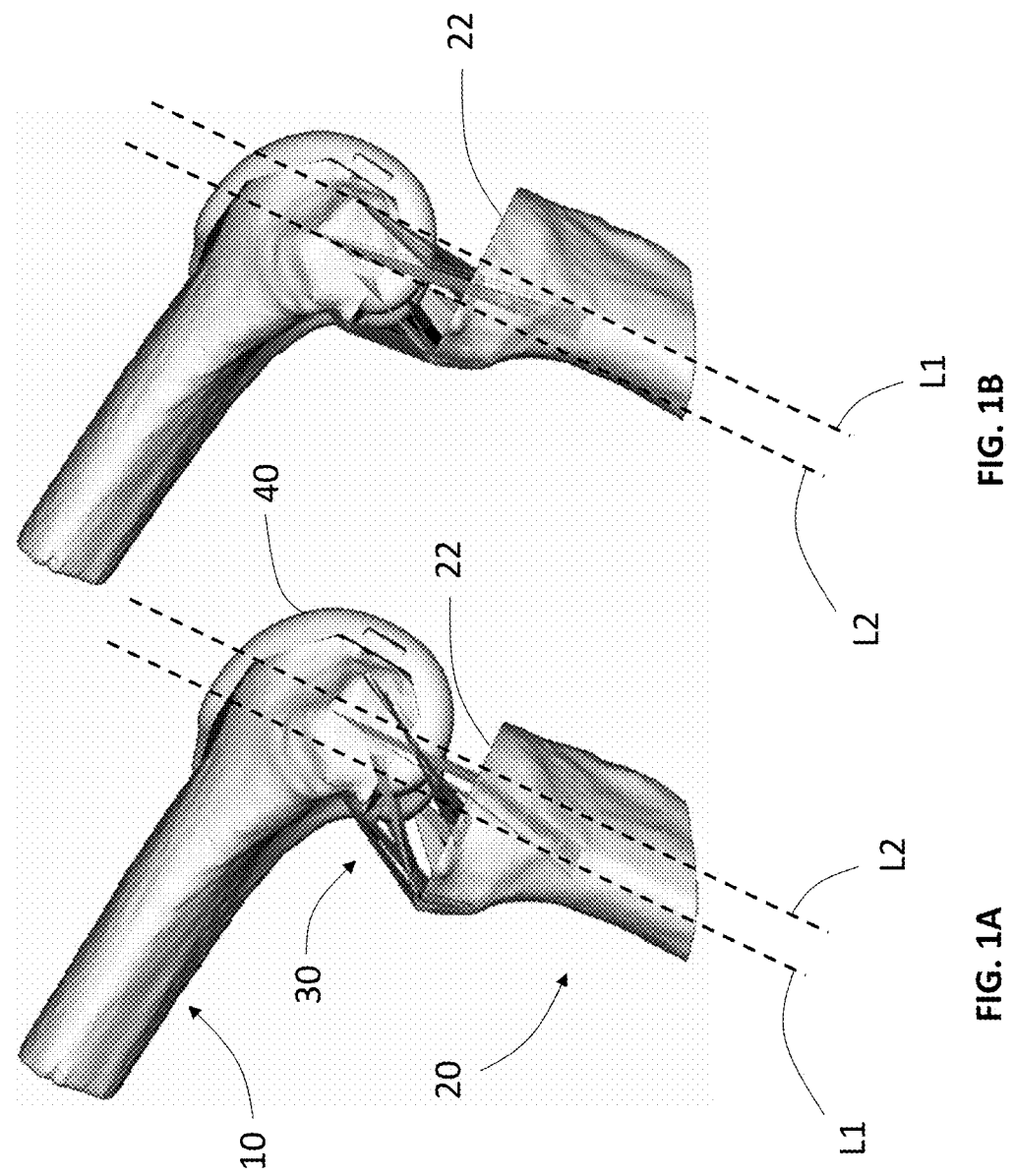
FIGS. 1A and 1B are side views of a knee joint translation in flexion.

Reference will now be made in detail to the various embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described. As used herein, the terms "implant trial" and "trial" will be used interchangeably and as such, unless otherwise stated, the explicit use of either term is inclusive of the other term. Similarly, the terms "implant" and "prosthesis" will be used interchangeably and as such, unless otherwise stated, the explicit use of either term is inclusive of the other term.

In describing preferred embodiments of the disclosure, reference will be made to directional nomenclature used in describing the human body. It is noted that this nomenclature is used only for convenience and that it is not intended to be limiting with respect to the scope of the invention. For example, as used herein, the term "distal" means toward the human body and/or away from the operator, and the term "proximal" means away from the human body and/or towards the operator.

The present disclosure includes a surgical system ("the System") and a method for alerting a surgeon during a joint balancing procedure when the femur-tibia translation is beyond an acceptable threshold during joint distraction and assessment. While the system and method of the present application are generally discussed with reference to a knee joint, it should be understood that the System and methods disclosed here can be used with other joint procedures, such as the shoulder, elbow, ankle, etc. The System can track the joint during a total knee arthroscopy ("TKA") procedure, and provide surgical insights during various steps including ligament tensioning.

An embodiment of the present disclosure includes a surgical workflow to inform or notify a surgeon when a femur-tibia translation is beyond an acceptable threshold during joint distraction and assessment. Pre-resection steps include removal of osteophytes, removal of the ACL ligament, and collection of native knee range of motion ("ROM") and valgus-varus values to define a neutral zone for each flexion angle. The native ROM and valgus-varus values can be collected by performing a drop leg test. A load cell in boot or tibial fixation can be used to measure axial shear forces to determine a neutral condition.

In one embodiment a surgeon can make a tibial skim cut and insert a load sensor shim or a tensor to track contact points. The System is then capable of tracking the position of the load sensor shim or tensor relative to tibia. Load senor shim and/or tensor readings provide axial force and shear force, which are used to determine a neutral zone. For example, an ideal neutral condition has zero shear force.

An AP laxity assessment can be conducted to evaluate posterior cruciate ligament ("PCL") health and choose PCL stabilizing and/or substituting options such as posterior-stabilizing ("PS") or cruciate-substituting ("CS"), etc. For example, excessive rollback may indicate a compromised PCL, and a surgeon can choose a PS/CS design. In one embodiment, the System provides a change implant notification to alert the surgeon to select a different implant by monitoring roll-back.

A surgeon can perform a tibial resection depending on the surgical workflow. Following that, a surgeon can conduct mid-resection joint assessment during which the System monitors femur position relative to the tibia as the surgeon distracts the joint. The position of the femur in anterior-posterior, medial-lateral, interior-exterior, flexion-extension, etc. can be monitored. The System alerts the surgeon if the tibial translation distance is greater than a predetermined threshold. For example, an anterior or posterior translation of the tibia by +/−5 mm in flexion can serve as the predetermined threshold as shown in FIG. 1. The translation distance of the tibia and femur by tracking anatomic markers such as tibial and femoral mechanical or anatomic axes. In another example, the anterior or posterior translation of the tibia by +/−8 mm in extension can serve as the predetermined threshold as shown in FIG. 2.

Figure 12:
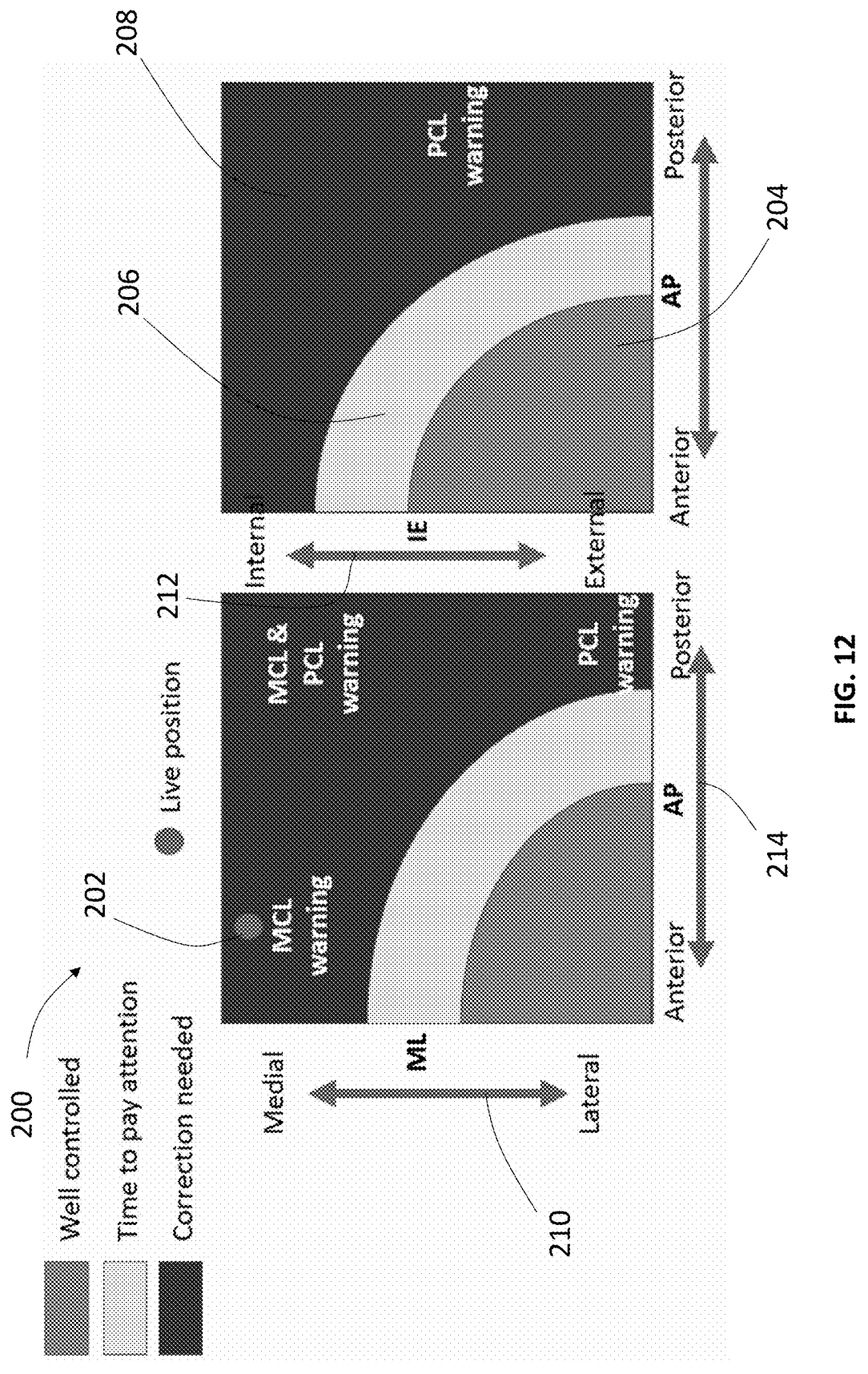
FIG. 12 is a schematic view of a translation notification screen.

The System alerts a surgeon if a femur position relative to the tibia leads to ligament transition zone exceeding a pre-determined threshold from neutral as shown in FIG. 12. For example, a pre-determined distance greater than 1 mm from a target zone will trigger the alert. This pre-determined distance can be set according to surgeon preference and/or determined from data sets, and 1 mm is merely an example for a particular surgery. The alert can be audible, visual, haptic, etc. A ligament model library (with or without PCL) complied from kinematic sensitivity data studies is used to provide alerts for over-stretched ligaments. For example, a library of virtual knee models is developed from cadaveric studies as more fully disclosed below. Tibial and femoral bone geometries are segmented from standard CT scans. All major soft tissues around the knee including, superficial medial collateral ligament ("sMCL"), deep medial collateral ligament ("dMCL"), lateral collateral ligament ("LCL"), PCL, oblique popliteal ligament ("OPL"), etc., are included in the model. Joint loads on the medial and lateral condyles can be collected at 5 lbf increment at flexion angle of 0, 10, 45 and 90 degrees. Soft tissue properties including slack length and linear stiffness are calibrated to match the measured joint loads versus displacement at 10- and 90-degree flexion. The resulting soft tissue properties are validated using the 45-degree flexion load vs displacement data. A sensitivity study on load-gap is performed for main relative positioning parameters including AP (±5 mm) and ML translation (±3 mm), IE rotation (±10 degree) and flexion angle (±5 degree). A transition gap at which the nonlinear laxity curve changes from low stiffness to high stiffness is used to assess sensitivity. The values noted above are exemplary for a particular surgical procedure, and may be modified based on surgeon preference.

The System can recommend gap corrections if the femur has excessive translation or rotation relative to the tibia. The System can identify and alert the surgeon when a ligament is stretched beyond a pre-determined threshold. The System can indicate the impact of osteophyte removal on ligament length and tension.

A robotic ligament balancing system at several flexion and extension poses (for example: balancing at 0, 45, and 90 deg) can be used to generate virtual ligaments that can then be simulated in the System. The data includes bone positions and the loads generated. A model is created based on the ligament attachment points of the specific patient. Input for this model will be the data from step 1 (example: 0 and 90 deg). A single pose of step 1 is used to confirm the output of the model is correct (example: 45 deg). If the validation is acceptable then the System can proceed to the next step; if not the System will need to have more input data. The trained model includes various implant position options entered. This data is preset based upon mechanical alignment, anatomical alignment, or other surgeon preferences. A simulation is completed for various combinations of implant positions. Output include the loads for each implant position.

The surgeon receives a display of the expected loads for various implant positions. The load ranges are color coded to preferred values. An ideal position are selected and displayed. The surgeon can then adjust the plan and see how the loads would vary with the changes to the positions.

A surgeon stress test establishes a patient-specific soft tissue envelope at multiple flexion angles. A sensor or load cell is placed inside or outside the joint along with kinematics measured using robotic tracker to load the joint up to the patient-specific soft tissue envelope to establish load versus gap curve for each compartment at each flexion angle.

Step 2 includes creating a real-time patient specific knee model. Ligament insertion sites are identified from a CT scan and represented with multiple bundles of nonlinear springs. All structurally important ligaments are included such MCL, LCL, PCL, OPL, etc. A rigid body framework is used to calibrate ligament properties. At each flexion angle, robotic kinematics are applied to the virtual model. Ligament properties are optimized until resultant forces match measured loads within a given tolerance for n−1 flexion angles—i.e., 0°, 10°, 20° and 90° laxity curves are used for calibration. Data from one flexion angle is reserved for model validation—i.e., 45° laxity curve is used to validate predictability of the model.

Step 3 includes creating a real-time planning parameter design of an experiment matrix (DOE). A DOE matrix is generated for tibial and femoral planning parameters. Surgeons can choose a center point of the DOE as Mechanical, Anatomical or User Defined and change the bounds of the DOE if desired. Each experiment can be simulated using the calibrated model. Compartment load at each flexion angle for each case in the DOE can be displayed and compared.

Step 4 includes planning parameters for a preferred outcome. Based on the DOE results, a color coded planning parameter based on load balance is used to expand the threshold or modify the target loads and visualize feasible cases. When visualizing one of the feasible cases, surgeons can adjust planning parameters live and see how the medial and lateral load change based on the DOE runs.

FIGS. 1A and 1B show anterior-posterior translations of a femur 10 and a tibia 20 in flexion. As shown in FIGS. 1A and 1B, femur 10 translates or shifts away from a tibial longitudinal axis L1 to an axis L2 along an anterior-posterior direction in flexion as permitted by joint ligaments 30. For example, femur 10 (shown with a femoral implant 40) translates posteriorly along resected distal surface 22 of tibia 20 in FIG. 1A, or translates anteriorly as shown in FIG. 1B. A distance between longitudinal axis L1 and an axis L2 defines the anterior-posterior translation.

Figures 2A, 2B:
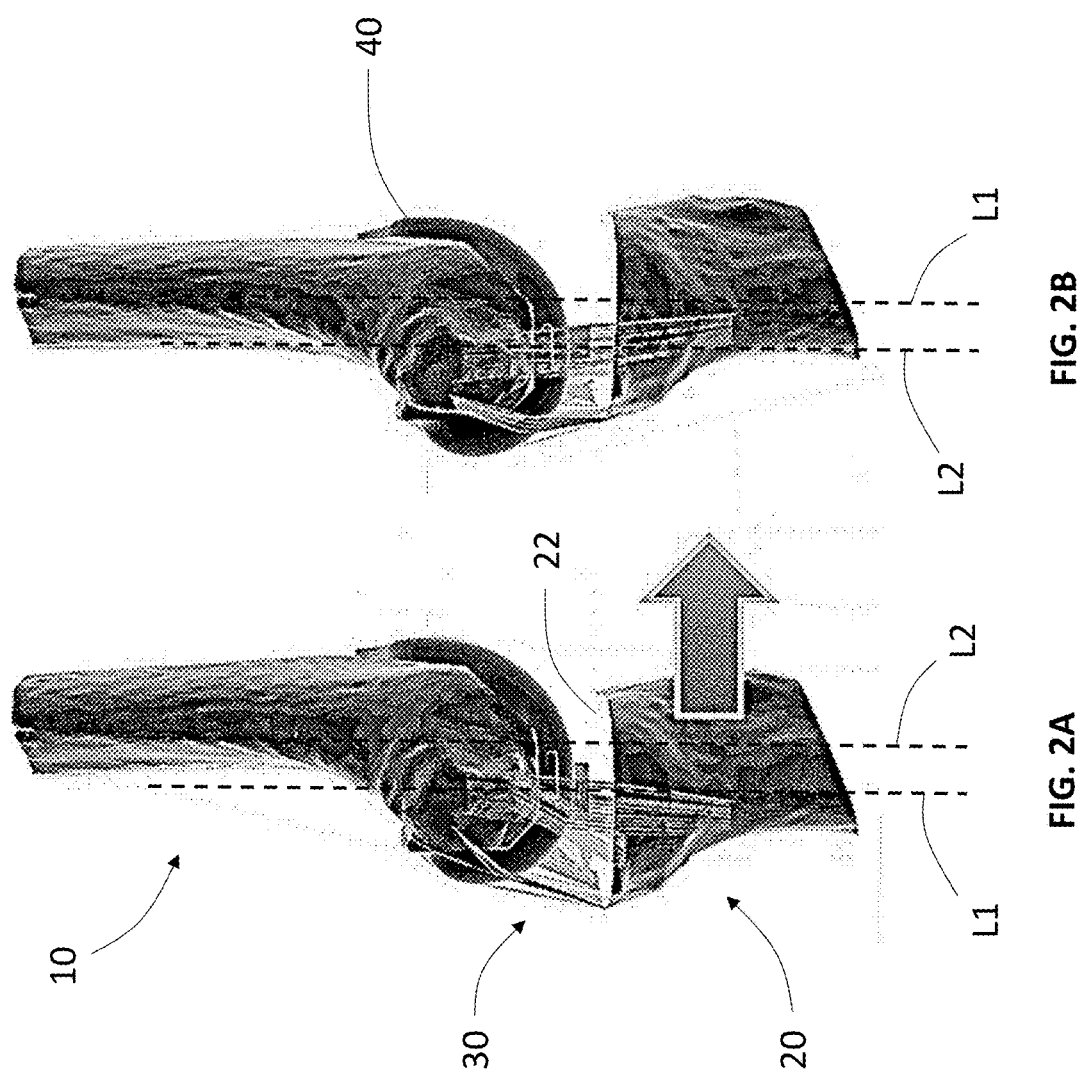
FIGS. 2A and 2B are side views of a knee joint translation in extension.

Referring now to FIGS. 2A and 2B, there is shown anterior-posterior translations of femur 10 and tibia 20 in extension. Femur 10 translates posteriorly along resected distal surface 22 of tibia 20 in FIG. 2A, or translates anteriorly as shown in FIG. 2B.

Figure 3:
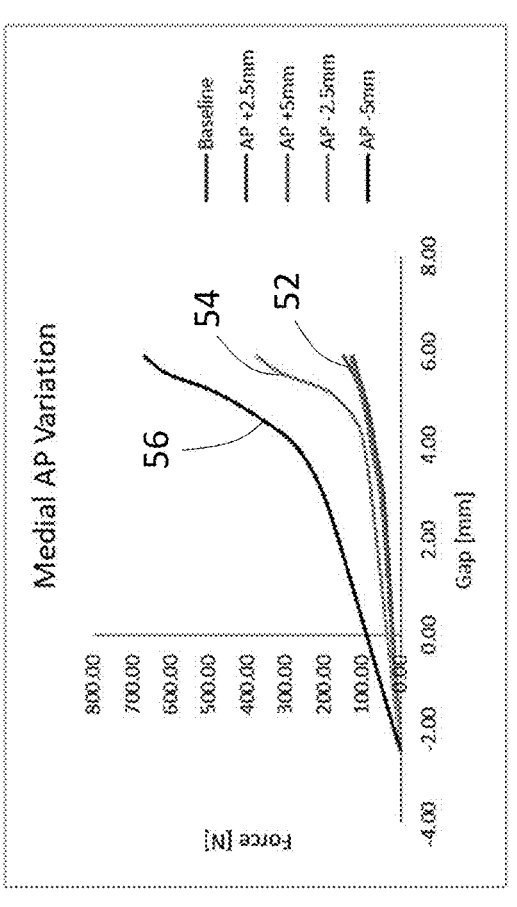
FIG. 3 is a graph showing force and joint gap on a medial knee joint at various anterior-posterior translations.

FIG. 3 shows a graph 50 comparing the impact of medial anterior-posterior translation on joint stiffness. A baseline stiffness 52 gradually increases as knee joint gap is increased. As shown in FIG. 3, the magnitude of anterior-posterior translation of knee joint directly impacts stiffness of the knee joint. For example, a medial anterior-posterior translation of −2.5 mm can significantly change the joint stiffness as shown by joint stiffness 54. This impact is directly proportional to the magnitude of translation as shown by joint stiffness 56 caused by a medial anterior-posterior translation of −5 mm. Similarly, lateral anterior-posterior translation impacts (i.e., increases) a baseline knee joint stiffness 62 as shown in graph 60 of FIG. 4. For example, a lateral anterior-posterior translation of −5 mm has a greater impact on baseline stiffness than a lateral anterior-posterior translation of −2.5 mm as shown by joint stiffness 66 and joint stiffness 64, respectively, in FIG. 4.

FIG. 5 shows a graph 70 comparing simulated joint stiffness derived from a virtual knee model according to an embodiment of the present disclosure. As more fully explained below, a virtual knee model is created to simulate knee kinematics and identify transition loads. As shown in FIG. 5, simulated knee stiffness varies (increases) as joint translation increases. For example, a joint translation of greater magnitude has a greater impact on knee stiffness as shown by stiffness 74 and 72.

Figures 6, 7:
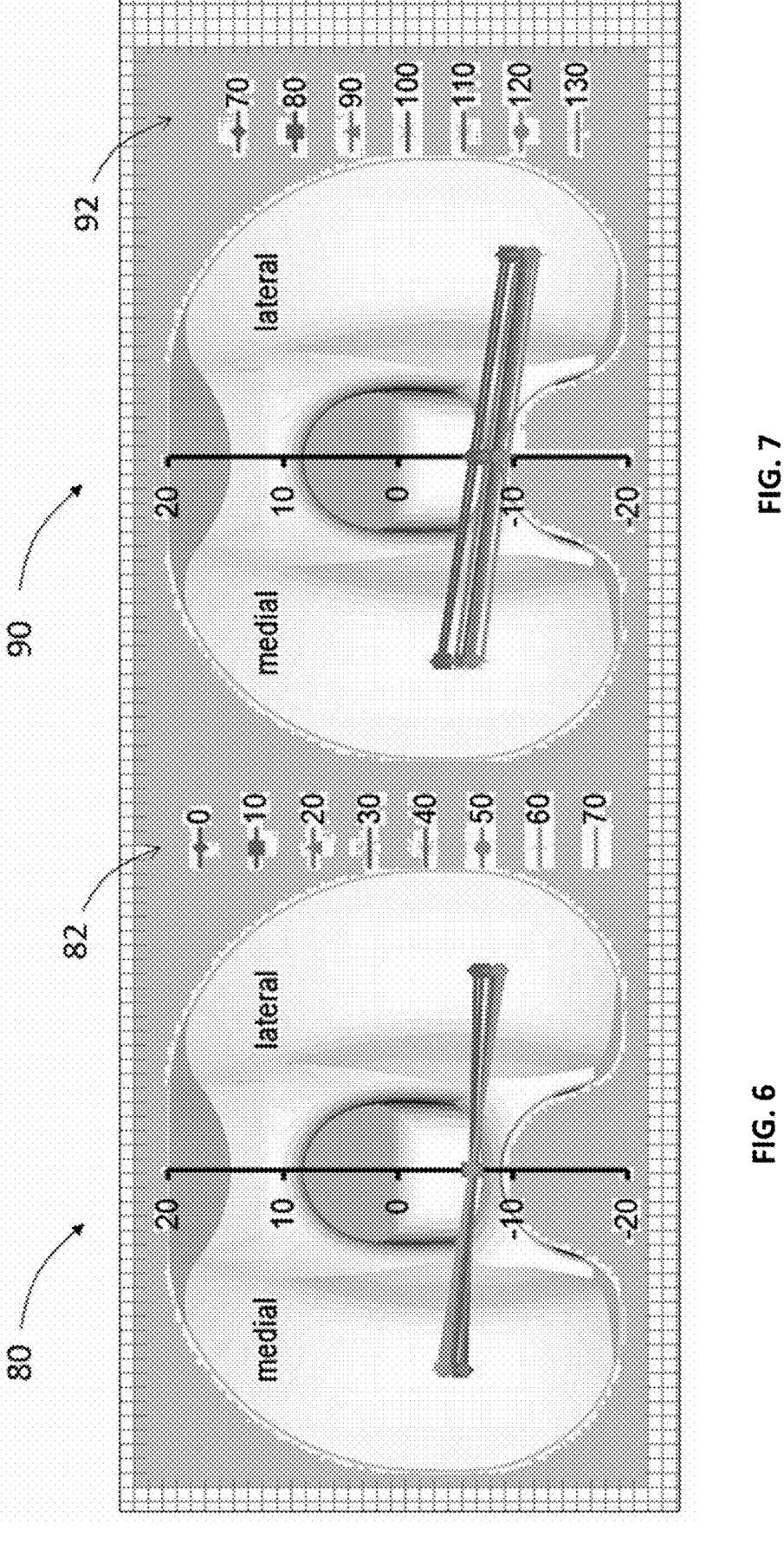
FIGS. 6 and 7 are schematic views of tibio-femoral contact during active and passive lateral flexion angles, respectively.
Figure 8:
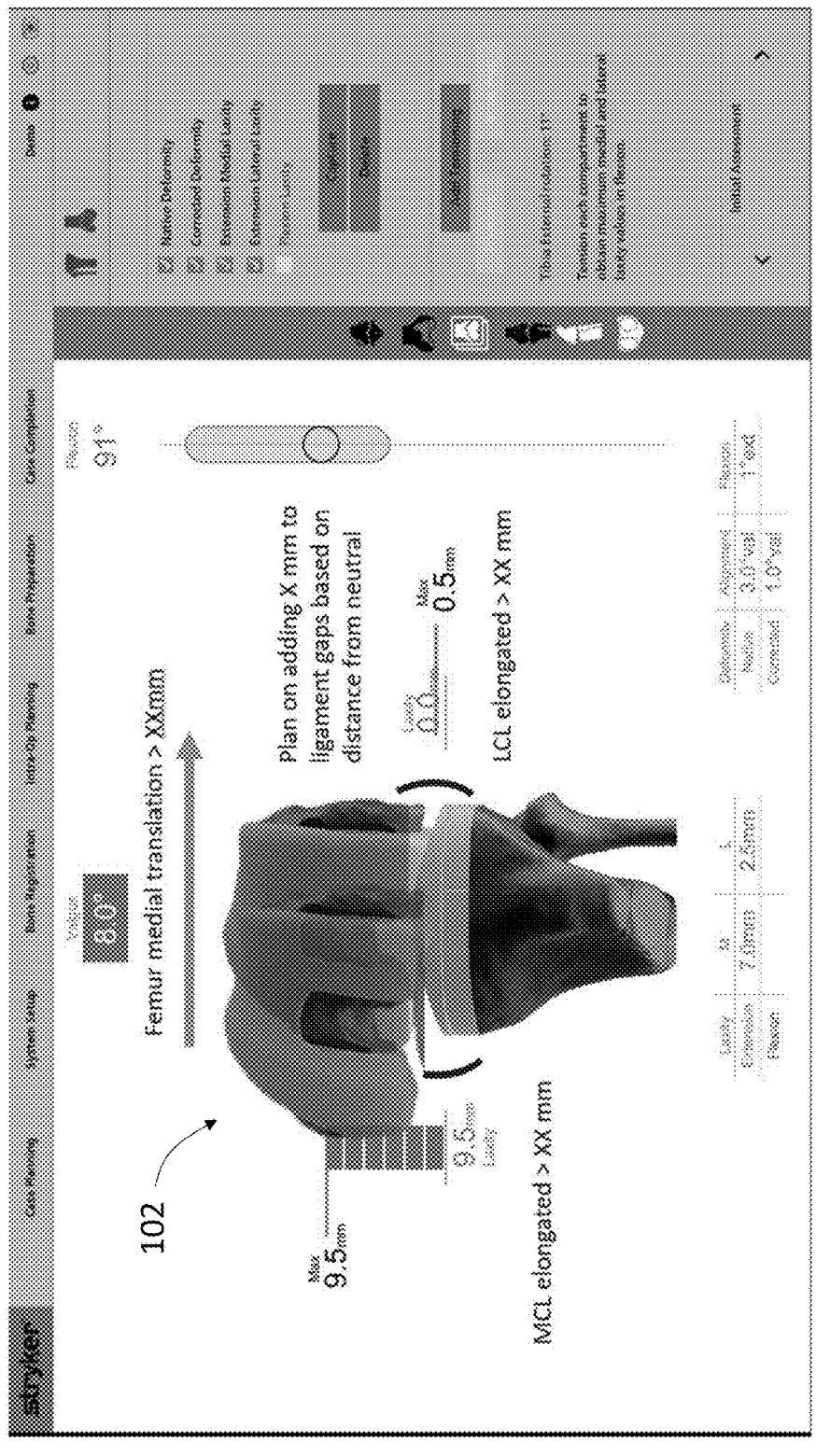
FIG. 8 is a schematic view of a user interface showing a femoral medial translation in a first position.

Cruciate kinematics can be evaluated by comparing tibio-femoral contact from active and passive lateral radiographs taken at varying flexion angles to evaluate post-operative rollback. For example, FIGS. 6 and 7 show tibio-femoral contact points 80 and 90 at varying knee flexion angles 82, 92.

Figure 9:
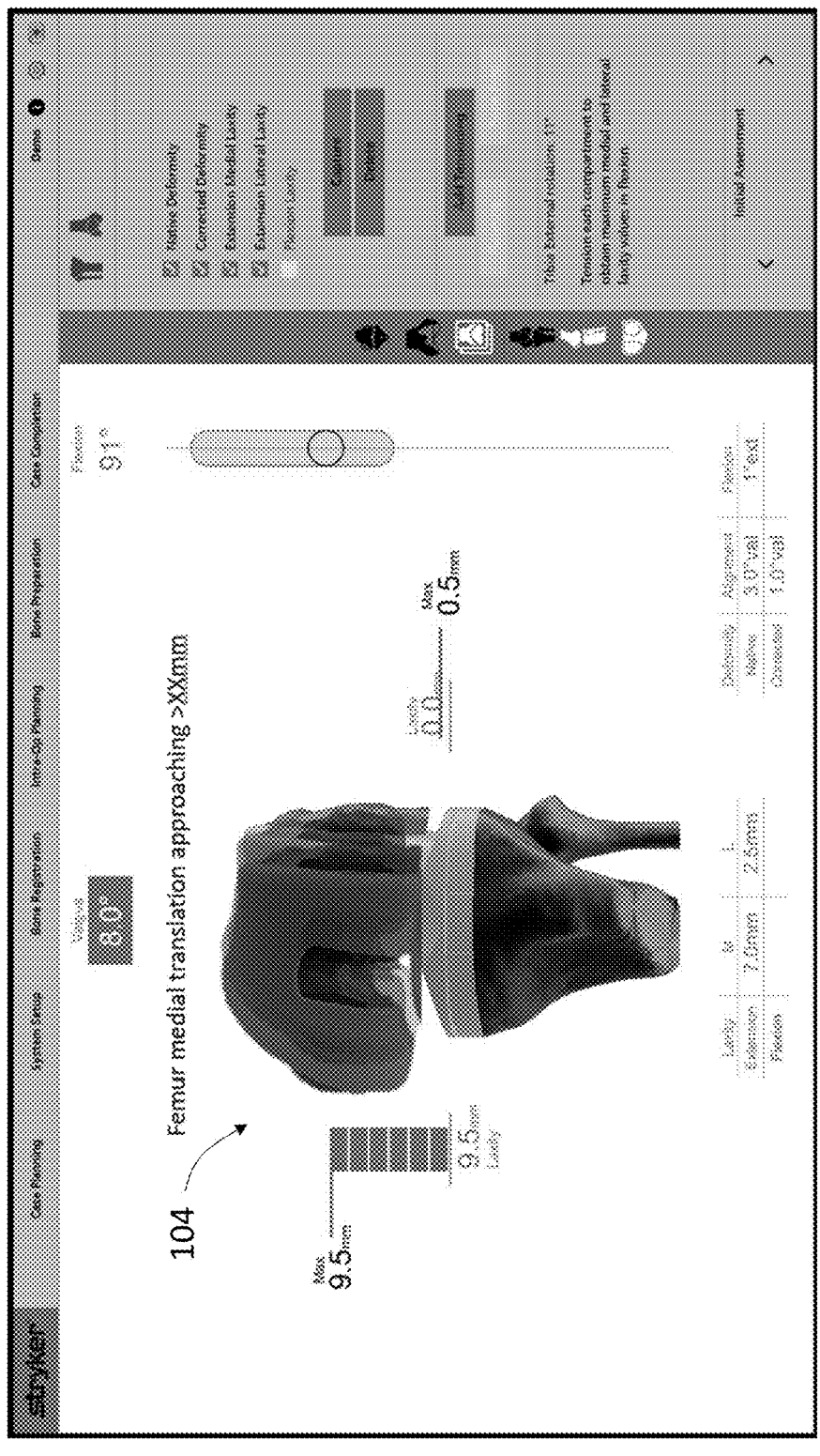
FIG. 9 is schematic view of the user interface showing the femoral medial translation in a second position.
Figure 10:
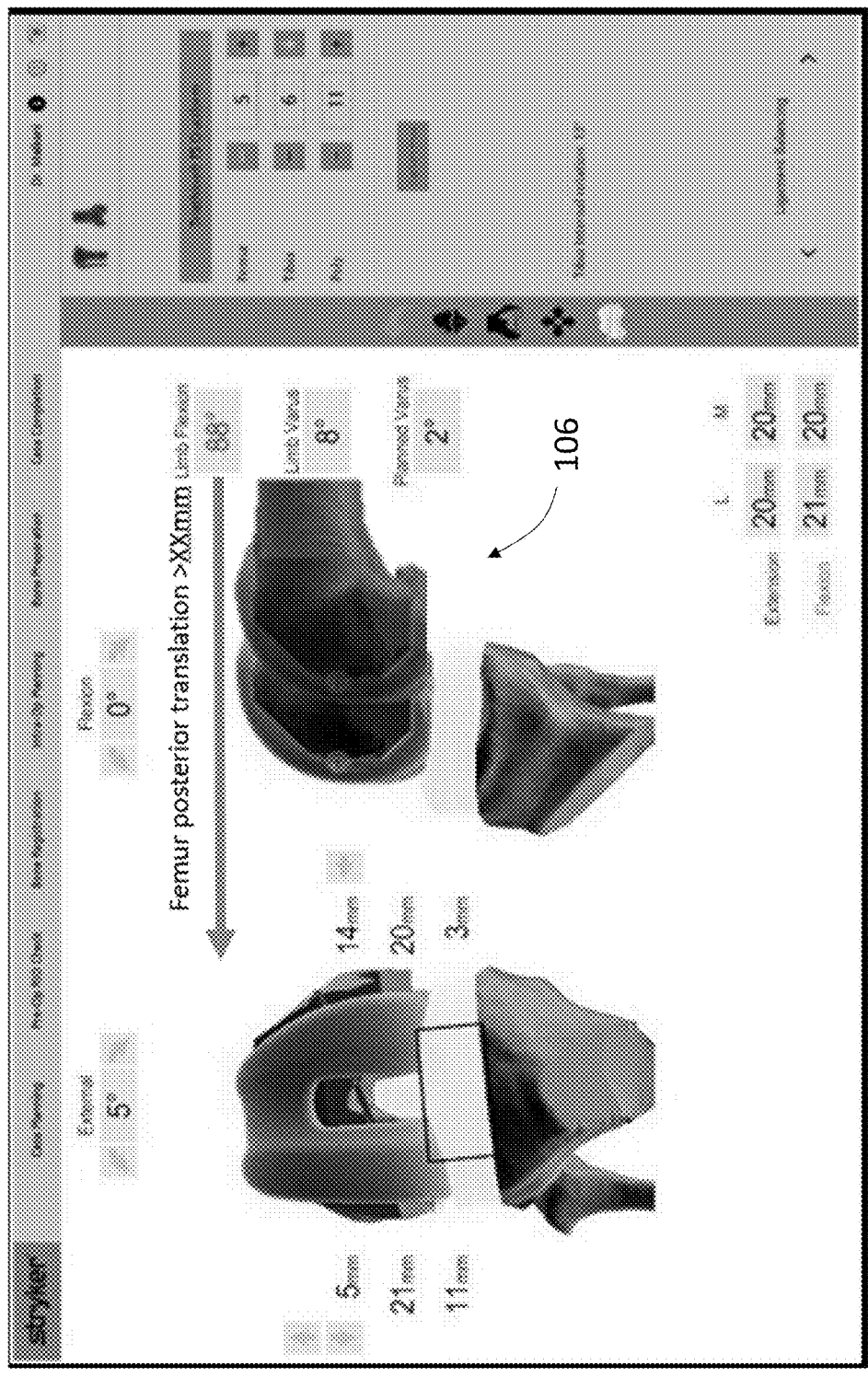
FIG. 10 is a schematic view of the user interface showing a femoral posterior translation in a first position.
Figure 11:
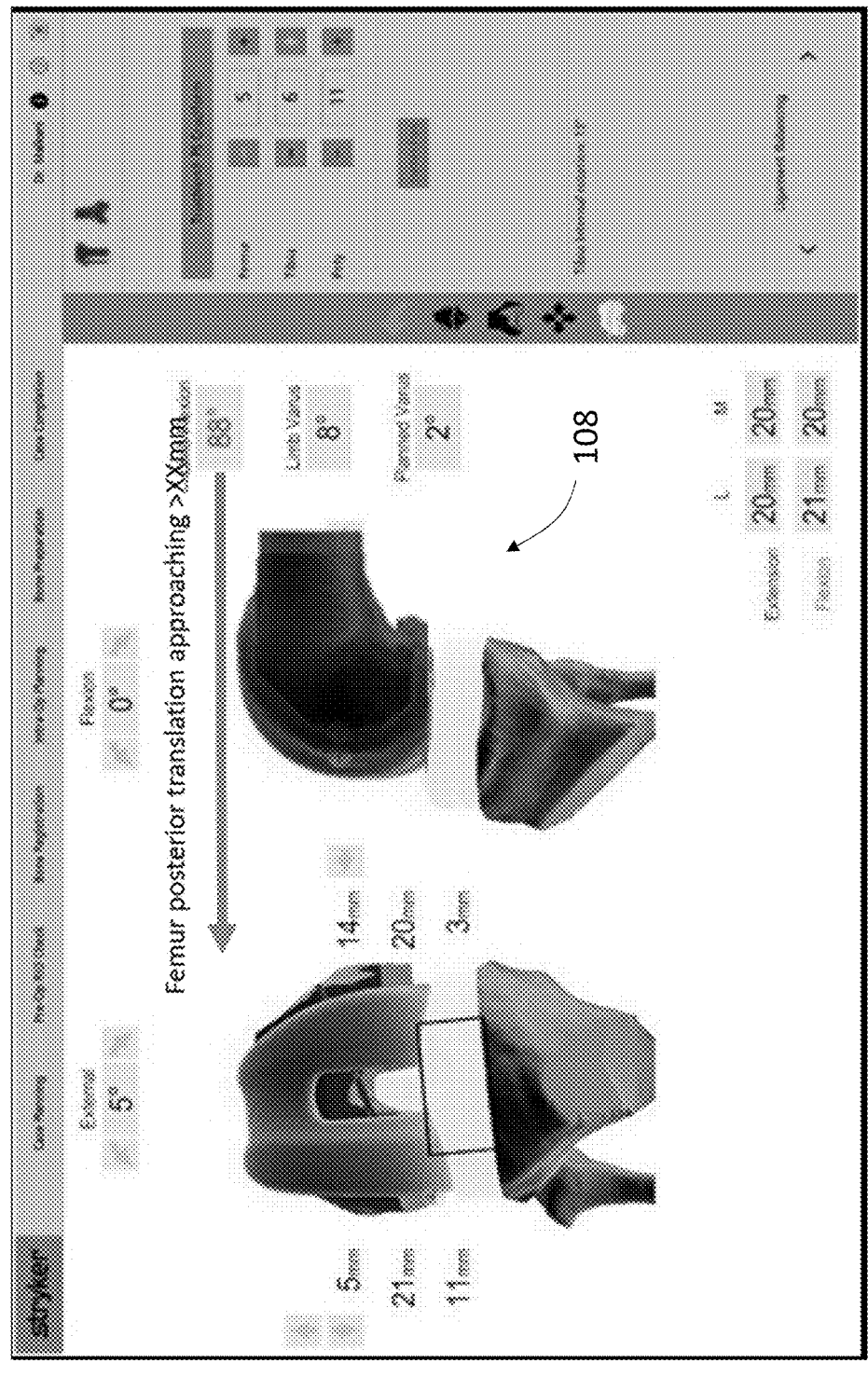
FIG. 11 is schematic view of the user interface showing the femoral posterior translation in a second position.

Referring now to FIGS. 8-11, there is shown a user interface 100 of the System according to an embodiment of the present disclosure. The System can identify and notify the surgeon (or an operator) when a femoral medial translation 102 exceeds a predetermined threshold as shown in FIG. 9. For example, the System may prompt the surgeon to add to the measured ligament gaps to account for joint translation. If a femoral medial translation 104 is within predetermined threshold, the System utilizes the measured ligament gaps as shown in FIG. 9. Similarly, the System will prompt a surgeon when anterior-posterior translation 106 of the femur exceeding predetermined thresholds as shown in FIGS. 10 and 11.

FIG. 12 shows a translation notification screen 200 of the System according to an embodiment of the present disclosure. Translation notification screen 200 can include a live position marker 202 indicating position along an anterior-posterior axis 214 and medial-lateral axis 210 or internal-external rotation axis 212 as shown in FIG. 12. The System alerts the surgeon when joint translation is within an acceptable region 204, a threshold region 206, or exceed a correction region 208. Thus, the System alerts the surgeon in real time to correct changes induced by joint translation.

Figure 13:
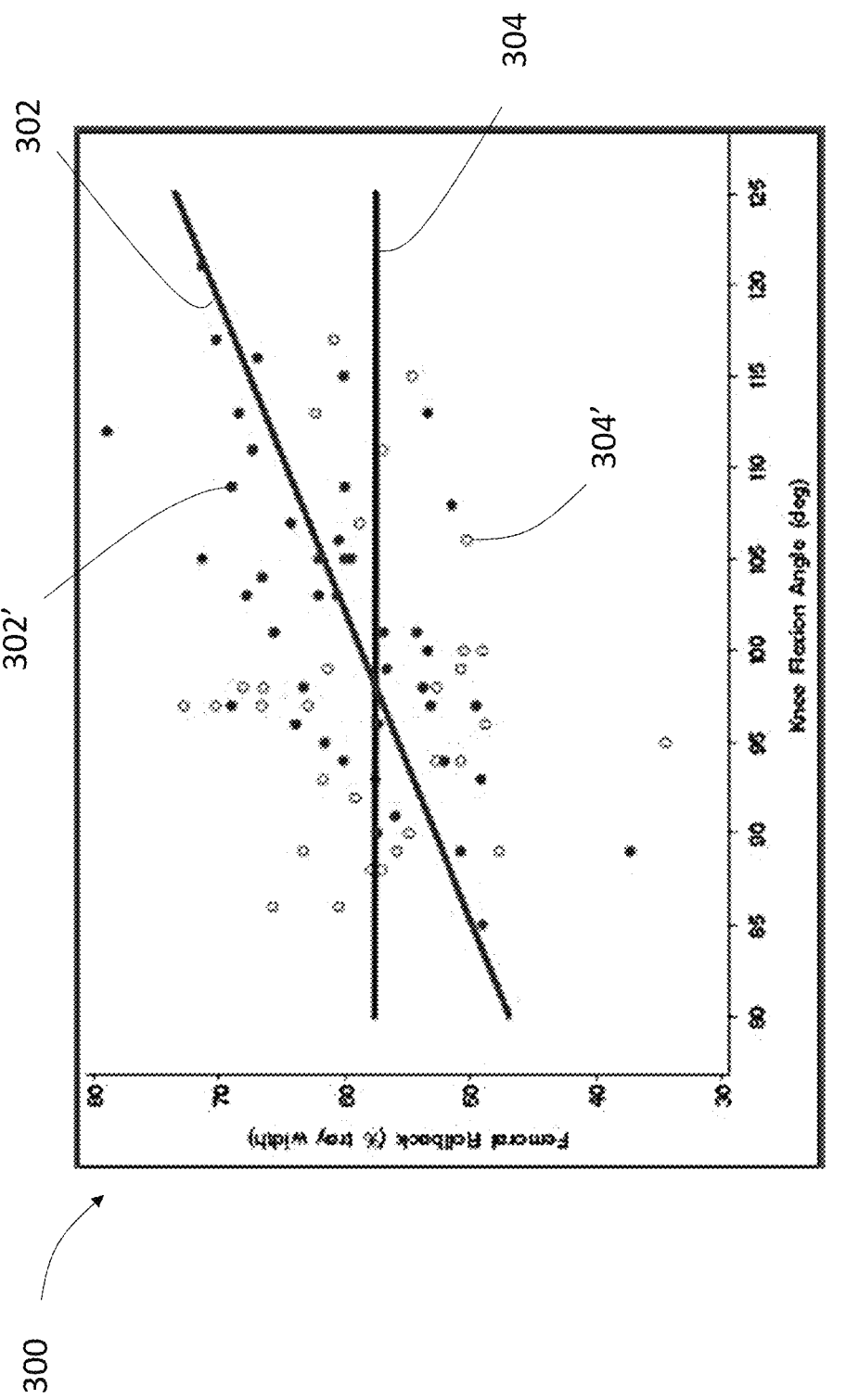
FIG. 13 is a graph showing knee flexion angle and femoral rollback.

FIG. 13 shows a graph 300 depicting post-operative knee flexion angle and femoral rollback for first and second groups of patients. A virtual knee model was utilized pre-operative and intra-operatively for the first group of patients. As shown in FIG. 13, femoral rollback measurements (measured as a percentage of tray width) 302' indicated positive linear correlation 302 with knee flexion angle. Conversely, no association of femoral rollback 304' with knee flexion angle was observed 304 for the second group of patients.

Figure 14:
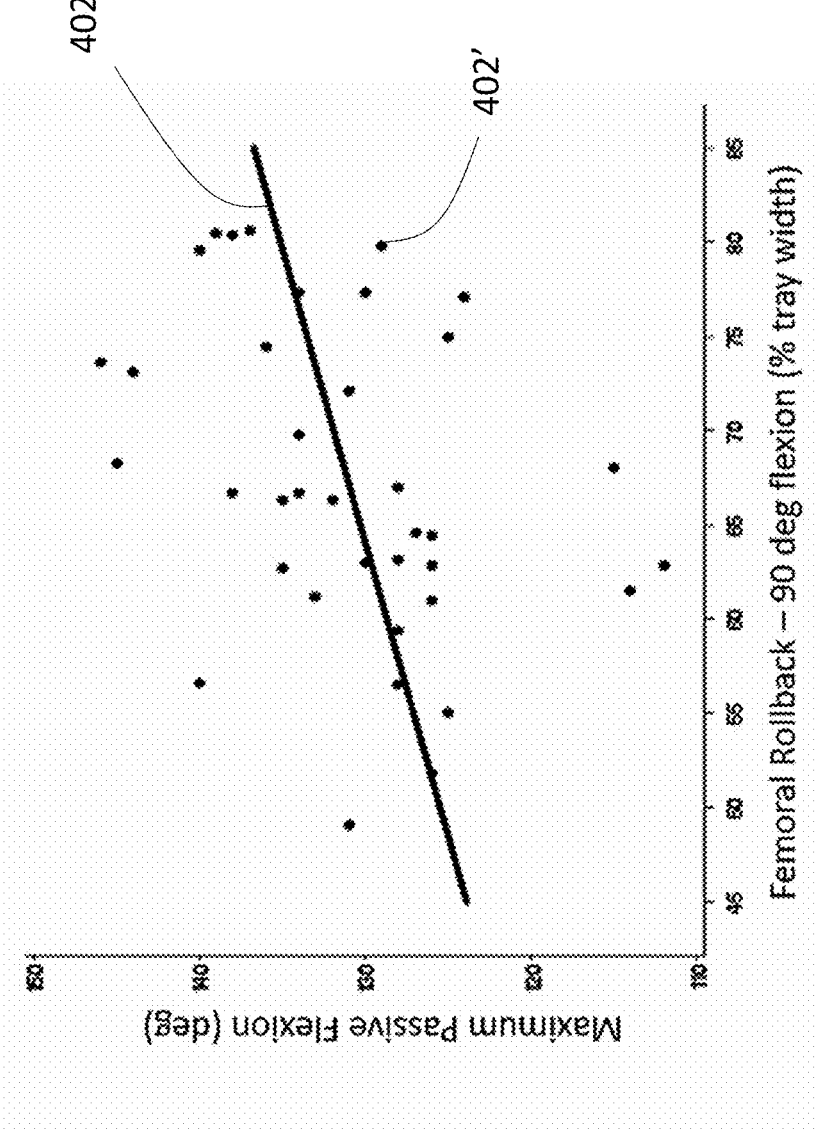
FIG. 14 is a graph showing femoral rollback and maximum passive flexion.

FIG. 14 shows a graph 400 depicting femoral rollback and passive flexion angle for patient in the first group 402', 402. As shown here, simulations from the virtual knee model in conjunction with real-time tracking system can be used to evaluate femoro-tibial kinematics to successfully predict post arthroplasty kinematic prior to implantation. A table 410 (FIG. 15) shows a post-operative comparison between the first and second group of patients. As shown here, an improved posterior cruciate modulated rollback is associated with an increase in radiographically measure active knee flexion of up to 16 degrees.

Figure 16:
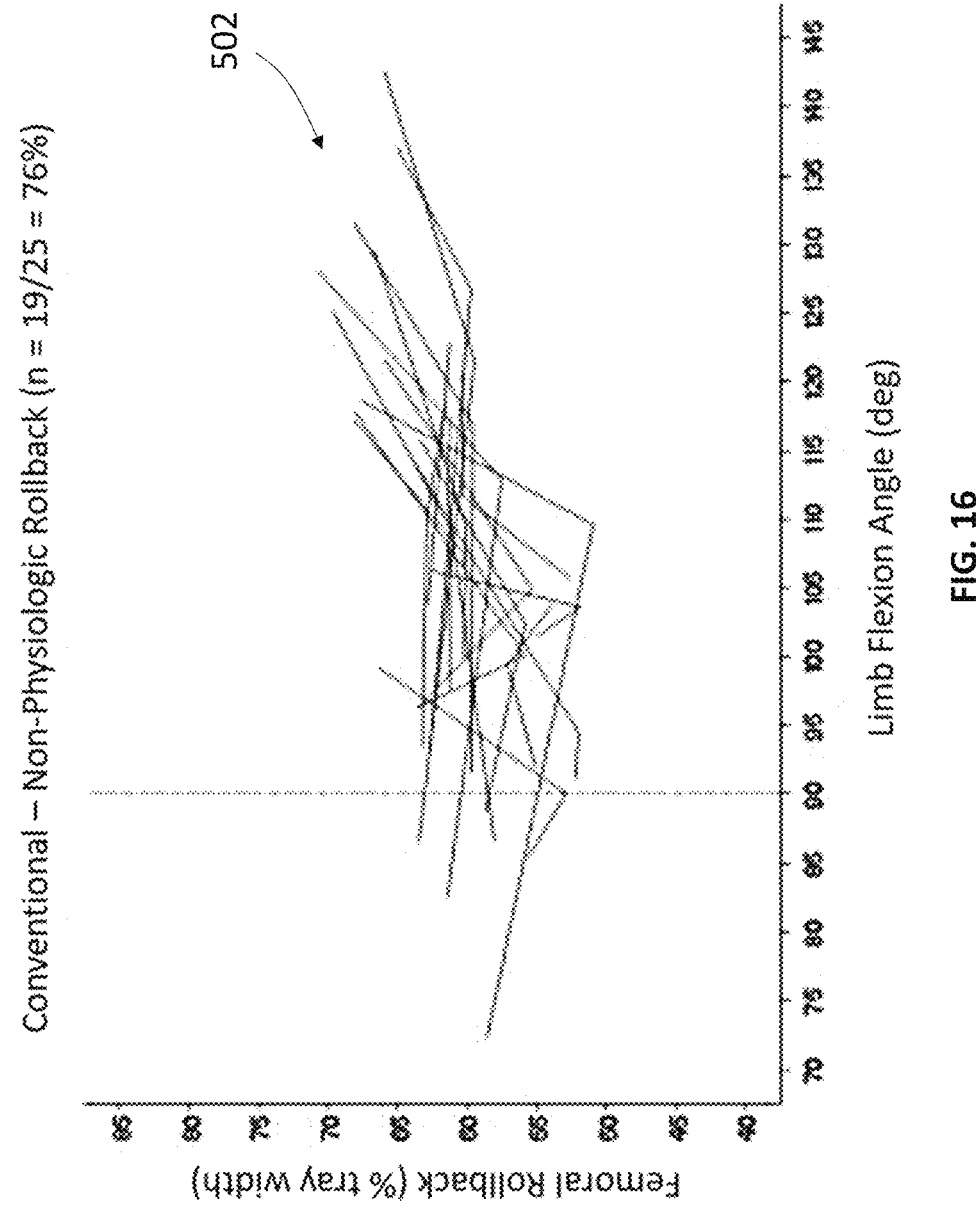
FIG. 16 is a graph showing knee flexion angle and femoral rollback for a first group of patients.
Figure 17:
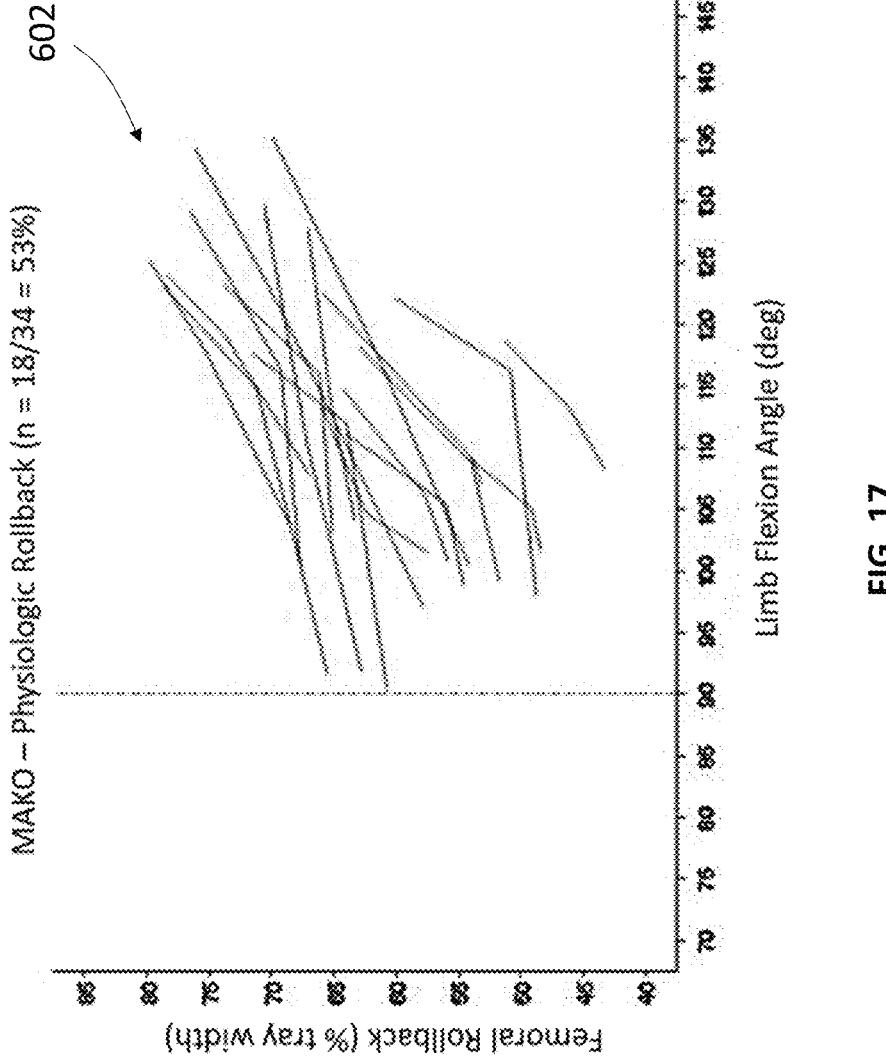
FIG. 17 is a graph showing knee flexion angle and femoral rollback for a second group of patients.

Referring now to FIGS. 16 and 17, there are shown graphs 500 and 600 illustrating patient post-operative recovery. Graph 600 shows post-operative recovery 602 (flexion angle vs. femoral rollback) for patients in the first group and graph 500 shows post-operative recover 502 for patients in the second group. As shown in these graphs, patients in the first group exhibit a monotonic pattern of increasing rollback absent of any paradoxical motion in more than twice the proportion of patients as the second group. The average maximum active flexion angle for the first group was greater than the second group.

Figure 4:
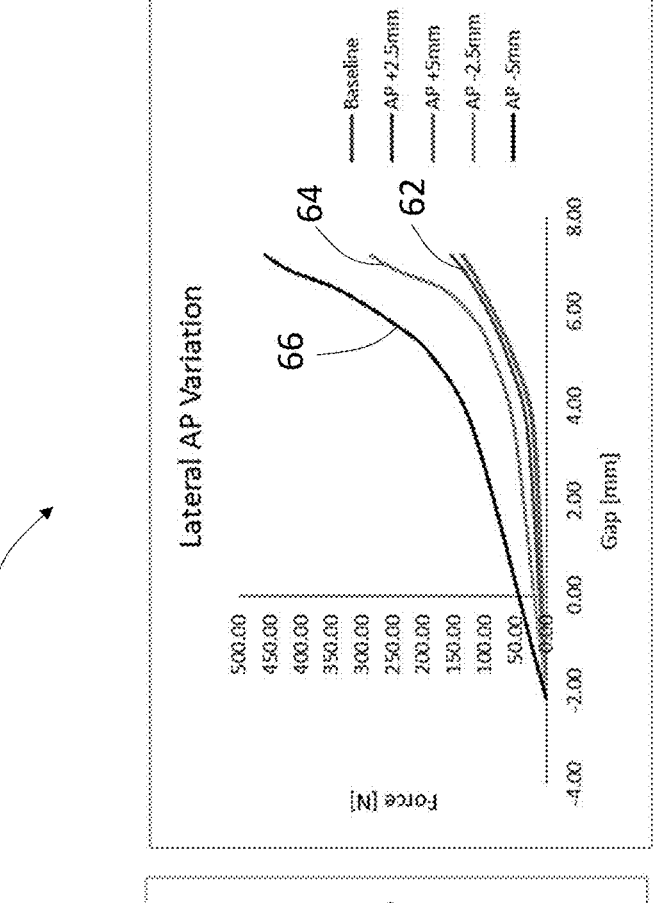
FIG. 4 is a graph showing force and joint gap on a lateral knee joint at various anterior-posterior translations.
Figure 18:
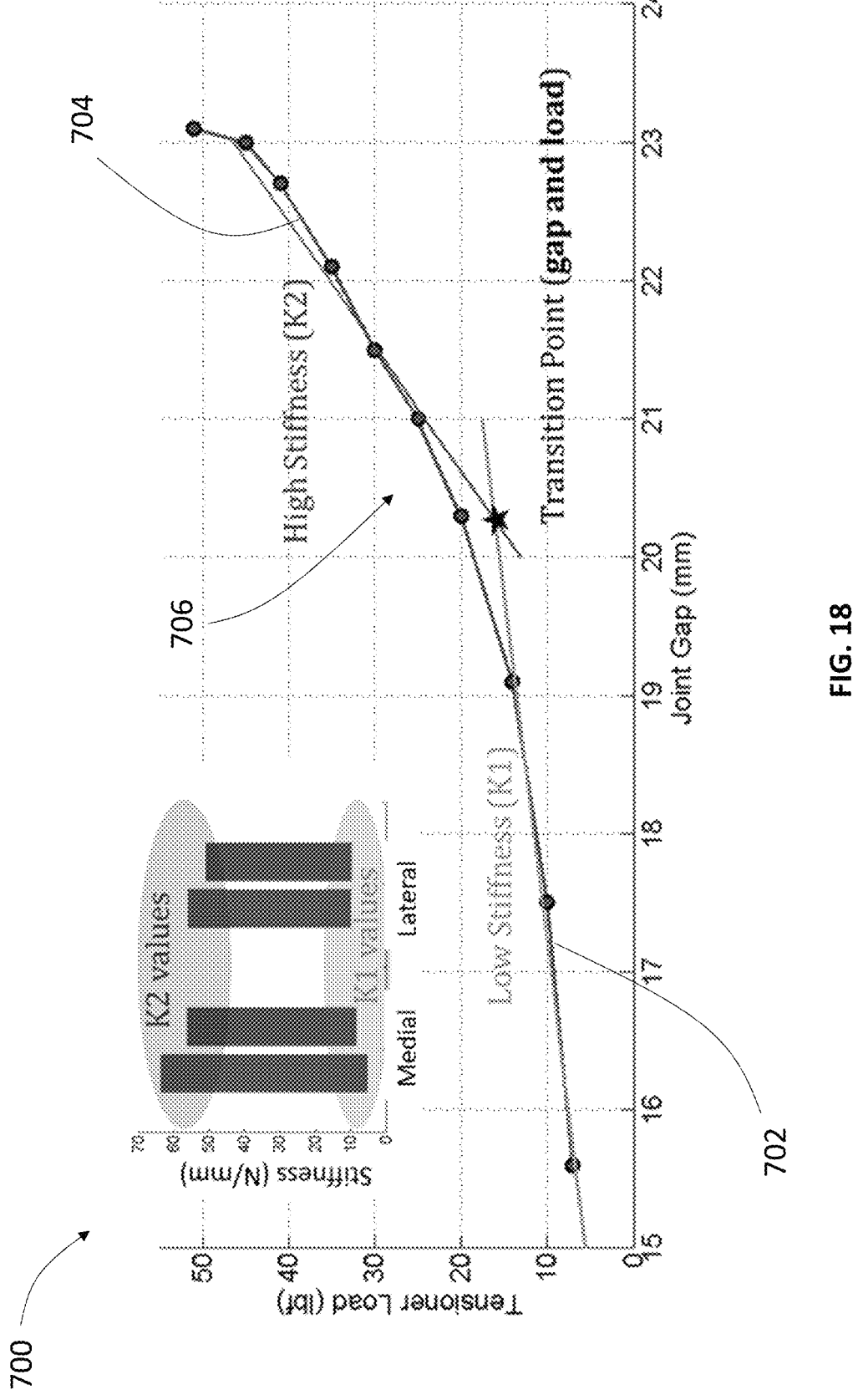
FIG. 18 is a graph showing joint tension load and joint gap.

FIG. 18 shows a graph 700 illustrating knee joint stiffness. As shown here, knee joint stiffness exhibits three distinct regions: a low stiffness region 702, a transition region 706 and a high stiffness region 704. As shown in graph 800 of FIG. 19, low stiffness region 802 indicates that the knee joint is too loose whereas high stiffness region will result in the knee joint being too tight. Thus, the transition region 706, 806 between the low stiffness region and high stiffness region represent the target knee joint stiffness. Joint translation can significantly change target knee joint stiffness—i.e., transition region 706, 806 as best shown in FIGS. 3 and 4 above.

Figure 19:
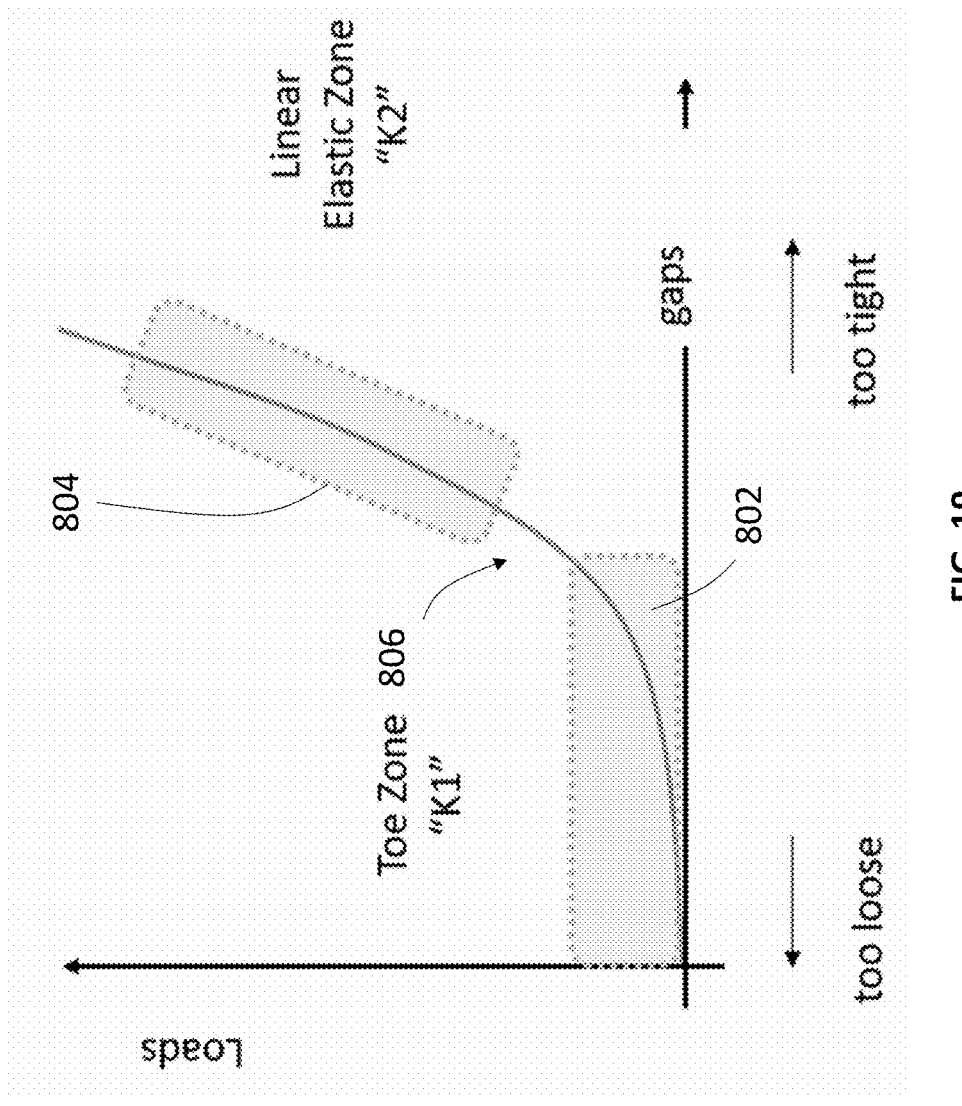
FIG. 19 is a graph showing joint tension load and joint gap.
Figure 20:
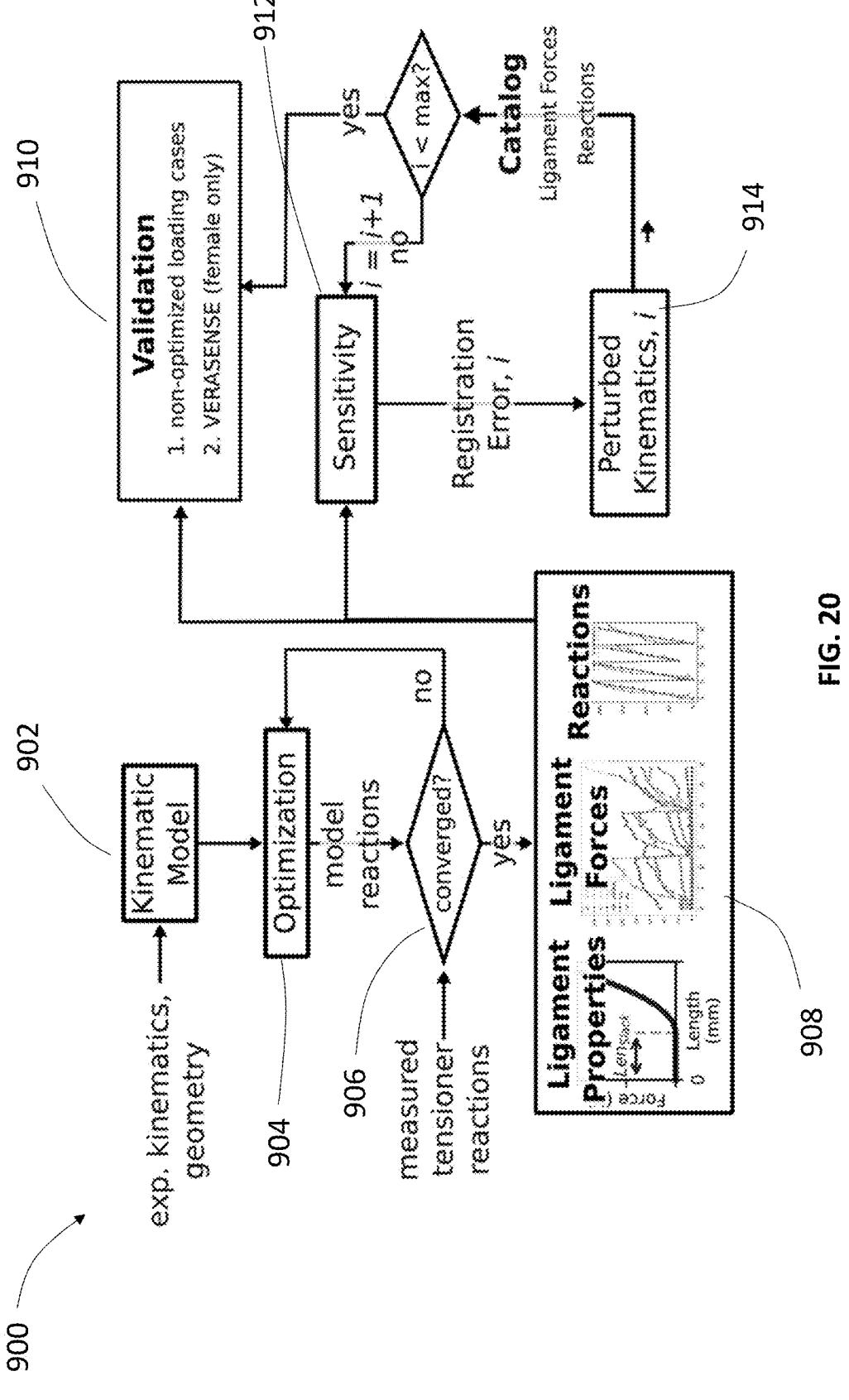
FIG. 20 is a flowchart showing steps for creating a virtual joint model.

FIG. 19 shows a flow chart 900 to create and utilize a virtual knee model based on laxity according to an embodiment of the present disclosure. Knee kinematics and geometry from experiments (cadaveric studies, etc.) are used to create a virtual knee model in step 902. A library of virtual knee models with patient-specific soft tissue properties to simulate sensitivity of medial and lateral joint gap to relative positioning parameter is created. The measured sensitivity can standardize laxity assessment practices and develop guided robotic assessment tools. All major soft tissues around the knee including, sMCL, dMCL, LCL, PCL, OPL, etc., are included in the virtual model. Joint loads on the medial and lateral condyles are collected at 5 lbf increment at flexion angle of 0, 10, 45 and 90 degree. Soft tissue properties including slack length and linear stiffness are calibrated to match the measured joint load-displacement at 10 and 90 degree flexion. The resulted soft tissue properties are validated using the 45 degree flexion load-displacement data in step 910. A sensitivity study on load-gap is performed for main relative positioning parameters including AP (±5 mm) and ML translation (±3 mm), IE rotation (±10 degree) and flexion angle (±5 degree) in step 912. Transition gap at which the nonlinear laxity curve changes from low stiffness to high stiffness is used to assess sensitivity. The virtual model is optimized in step 904 and checked for convergence in step 906. The virtual model can then be used to simulate and predict ligament properties, ligament forces and reactions as shown in step 908.

Furthermore, although the invention disclosed herein has been described with reference to particular features, it is to be understood that these features are merely illustrative of the principles and applications of the present invention. While the embodiments of the present disclosure are generally described with reference to the knee joint, it should be understood that these embodiments can be used for all other joints including the hip and shoulder. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A method of determining resection depths for a knee arthroplasty procedure using a surgical system including a sensor and a user interface, the method comprising:
   determining a joint translation threshold, the joint translation threshold being defined as a translation distance of a femur with respect to a tibia;
   determining a joint translation of the femur with respect to the tibia during a joint gap measurement using the sensor, wherein the joint translation comprises at least one of an anterior-posterior translation, a medial-lateral translation, or an internal-external rotation of the femur with respect to the tibia;
   setting a final joint gap measurement, wherein the joint translation is less than or equal to the joint translation threshold;
   alerting a user via the user interface of the surgical system when the joint translation exceeds the joint translation threshold during the joint gap measurement, and
   determining knee resection depths based on the final joint gap measurement.

2. The method of claim 1, wherein the joint translation is defined as a distance between a femoral axis and a tibial axis.

3. The method of claim 2, wherein the femoral axis is any of a femoral mechanical axis and a femoral anatomical axis.

4. The method of claim 3, wherein the tibial axis is any of a tibial mechanical axis and a tibial anatomical axis.

5. The method of claim 1, wherein the translation distance is defined by the anterior-posterior translation of the femur with respect to the tibia.

6. The method of claim 1, wherein the translation distance is defined by the medial-lateral translation of the femur with respect to the tibia.

7. The method of claim 1, wherein the translation distance is defined by the internal-external rotation of the femur with respect to the tibia.

8. A method of determining resection depths for a knee arthroplasty procedure using a surgical system comprising at least one tracking sensor and a user interface, the method comprising:
   detecting, by the tracking sensor, positions of a femur and a tibia during a joint gap measurement;
   calculating, by the surgical system, a joint translation of the femur relative to the tibia based on data received from the tracking sensor;
   determining, by the surgical system, a joint translation threshold defined as a maximum permissible translation distance between the femur and the tibia corresponding to a predetermined ligament tension range;
   comparing, by the surgical system, the calculated joint translation with the joint translation threshold;

generating, when the calculated joint translation exceeds the joint translation threshold, a visual, audible, or haptic alert via the user interface to prompt adjustment of joint distraction; and setting, when the calculated joint translation is less than or equal to the joint translation threshold, a final joint gap measurement and determining knee resection depths based on the final joint gap measurement from the tracking sensor, wherein the joint translation comprises at least one of an anterior-posterior translation, a medial-lateral translation, or an internal-external rotation of the femur relative to the tibia.

* * * * *